United States Patent
Plotts et al.

(10) Patent No.: US 7,313,485 B2
(45) Date of Patent: Dec. 25, 2007

(54) METHOD OF ESTIMATING OXIDATION PROGRESSION IN COATED TURBINE COMPONENTS

(75) Inventors: Kurt Augustus Plotts, Oviedo, FL (US); Malberto Fernandez Gonzalez, Orlando, FL (US); Andrew Jeremiah Burns, Orlando, FL (US)

(73) Assignee: Siemens Power Generation, Inc., Orlando, FL (US)

( * ) Notice: Subject to any disclaimer, the term of this patent is extended or adjusted under 35 U.S.C. 154(b) by 0 days.

(21) Appl. No.: 10/909,055

(22) Filed: Jul. 30, 2004

(65) Prior Publication Data

US 2006/0025936 A1 Feb. 2, 2006

(51) Int. Cl.
G01N 31/00 (2006.01)
(52) U.S. Cl. .......................... 702/34; 702/22
(58) Field of Classification Search ............... 702/23, 702/34; 700/175–176; 73/86
See application file for complete search history.

(56) References Cited

U.S. PATENT DOCUMENTS

| | | | |
|---|---|---|---|
| 5,963,880 A * | 10/1999 | Smith | 702/34 |
| 6,047,241 A * | 4/2000 | Sparago | 702/34 |
| 6,343,251 B1 | 1/2002 | Herron et al. | |
| 6,499,114 B1 | 12/2002 | Almstead et al. | |
| 6,556,956 B1 | 4/2003 | Hunt | |
| 6,587,754 B2 | 7/2003 | Hung et al. | |
| 6,706,319 B2 * | 3/2004 | Seth et al. | 427/190 |
| 6,718,283 B2 * | 4/2004 | Lanham et al. | 702/183 |
| 6,745,151 B2 * | 6/2004 | Marko et al. | 702/182 |
| 6,922,640 B2 * | 7/2005 | Vezzu et al. | 702/34 |
| 2002/0111749 A1 * | 8/2002 | Yang et al. | 702/34 |
| 2004/0108019 A1 * | 6/2004 | Schnell et al. | 148/509 |
| 2004/0230411 A1 * | 11/2004 | Zheng et al. | 703/6 |

FOREIGN PATENT DOCUMENTS

EP 1 227 22 A2 7/2002
EP 1 418 312 A2 5/2004

OTHER PUBLICATIONS

Ashwin Shah; "Development of Reliability Based Life Prediction Methods for Thermal and Enviromental Barrier Coatings in Ceramic Matrix Composites", Jun. 2001, pp. 1-22; XP002417180; [Retrieved from the Internet]: URL:http://gltrs.grc.nasa.gov/reports/2001/CR-2001-210760.pdf.

Dongming Zhu and Robert A. Miller; "Thermal-Barrier Coatings for Advanced Gas-Turbine Engines"; MRS Bulletin; Jul. 2000; pp. 43-47; Materials Research Society; XP002417179; Warrendale, PA, USA.

Dina Toma, Waltraut Brandl, Uwe Köster; "Studies on the Transient Stage of Oxidation of VPS and HVOF Sprayed MCrAlY Coatings"; Surface & Coatings Technology; 1999; pp. 8-15; vol. 120-121; XP001004808: ISSN: 0257-8972: Amsterdam, NL.

* cited by examiner

*Primary Examiner*—John Barlow
*Assistant Examiner*—Jonathan Moffat

(57) ABSTRACT

The claimed invention relates to a method for determining the extent of an oxidation reaction of a coated metallic turbine component within a turbine, comprising determining a plurality of reference oxidation rates for a plurality of locations on the turbine component for a plurality of different turbine operating conditions. The invention also relates to selecting an appropriate oxidation rate from a family of reference oxidation rate data and estimating the oxidation of the coated turbine blade or vane.

24 Claims, 4 Drawing Sheets

METHOD OF ESTIMATING OXIDATION PROGRESSION IN COATED TURBINE COMPONENTS

FIELD OF INVENTION

The present invention relates generally to determining the extent of oxidation progression of a coated system, more particularly, on a coated turbine component.

BACKGROUND OF THE INVENTION

Gas turbine engines are known to include a compressor section for supplying a flow of compressed combustion air, a combustor section for burning fuel in the compressed combustion air, and a turbine section for extracting thermal energy from the combustion air and converting that energy into mechanical energy in the form of a rotating shaft.

Modern high efficiency combustion turbines have firing temperatures that exceed about 2,700° F., and even higher firing temperatures are expected as the demand for more efficient engines continues. Many components that form the "hot gas path" combustor and turbine sections are directly exposed to aggressive hot combustion gasses, for example, the combustor liner, the transition duct between the combustor and turbine sections, and the turbine stationary vanes and rotating blades and surrounding ring segments. In addition to thermal stresses, these and other components are also exposed to mechanical stresses and loads that further wear on the components.

Furthermore, many of the cobalt and nickel based superalloy materials traditionally used to fabricate the majority of combustion turbine components used in the hot gas path section of the combustion turbine engine must be aggressively cooled and/or insulated from the hot gas flow in order to survive long term operation in this aggressive high temperature combustion environment.

Notwithstanding these protective efforts, the combustion turbine components nonetheless tend to suffer operational damage such as thermal fatigue, oxidation, corrosion, creep, foreign object damage, and the like, which typically causes cracking and spallation of the super-alloy substrate and/or protective ceramic coating. Since these high temperature resistant components are quite expensive, it is often desirable to repair or refurbish parts and extend useful life.

It is desirable during engine operation to have an accurate estimation of the amount of oxidation that the coated system has undergone in order to help determine when to repair or refurbish the component.

Accordingly, there is a need to have the ability to suitably estimate oxidation progression within coated turbine components as a function of predicted duty cycle and component thermal history.

SUMMARY OF THE INVENTION

One aspect of the invention involves a method for determining the extent of an oxidation reaction of a coated metallic turbine component within a turbine, comprising determining a plurality of reference oxidation rates for a plurality of locations on the turbine component for a plurality of different turbine operating conditions; obtaining a set of actual turbine operating conditions based on time or temperature; obtaining a plurality of turbine component operating temperatures from the set of actual turbine operating conditions; selecting an appropriate reference oxidation rate from the plurality of reference oxidation rates based on the actual turbine operating conditions; using the selected reference oxidation rate as the actual oxidation rate; and calculating an amount of oxidation present in the turbine component using the actual oxidation rate.

Another aspect of the invention involves a method for determining the extent of an oxidation reaction of a coated metal turbine component within a turbine, comprising: providing an aluminum comprising coating on a metal substrate; providing a family of reference oxidation rate curves for the aluminum comprising coating as a function of time and temperature; calculating an actual oxidation rate for the aluminum comprising coating during operation of the turbine as a function of time or temperature; creating a path dependent oxidation rate curve based upon the calculated actual oxidation reaction rate; comparing the path dependent oxidation rate curve with the family of oxidation reaction rate curves; selecting from the family of reference oxidation reaction rate curves, a curve that generally corresponds with the path dependent oxidation rate curve; and using the selected curve to approximate the extent of oxidation.

Yet another aspect of the invention involves a method of determining the extent of an oxidation reaction of a composition, comprising: determining a plurality of oxidation rates; having or being provided one actual rate; nselecting from a plurality of oxidation rate curves a curve that most closely matches to a curve representative of actual operating conditions; and using the curve to calculate the extent of oxidation

BRIEF DESCRIPTION OF THE DRAWINGS

The above mentioned and other concepts of the present invention will now be described with reference to the drawings of the exemplary and preferred embodiments of the present invention. The illustrated embodiments are intended to illustrate, but not to limit the invention. The drawings contain the following figures, in which like numbers refer to like parts throughout the description and drawings and wherein.

DETAILED DESCRIPTION OF THE INVENTION

The invention described herein employs several basic concepts. For example, one concept relates to a method of estimating the extent of the oxidation reaction in a coated metallic turbine component using operational data collected continuously from the turbine in which the component is located. Another concept relates to selecting an appropriate oxidation rate from a family of reference oxidation rate data and estimating the oxidation of the coated turbine component. Another concept relates to using an oxidation progression to determine the extent of oxidation.

The present invention is disclosed in context of use as a method for determining the extent of oxidation of metallic turbine components coated with a metallic oxidation resistant coating such as MCrAlY. The principles of the present invention, however, are not limited to use within gas turbine engines or to determining the extent of oxidation of metal turbine components coated with an MCrAlY composition and are not limited to oxidation reactions of metallic components. For example, this method could be used in other high temperature and non-high temperature environments to detect the extent of oxidation reaction to objects, such as steam turbines, chemical batteries, ceramic composites (such as the SiC—SiC composites), aero-thermal aircraft engines, electric generators, air or gas compressors, heavy duty diesel and gasoline engines, high temperature rocket combustors and thrust controllers, high temperature atmosphere re-entry devices, electroplating operations, and the like. For another example, a non aluminum comprising composition such as nickel based super-alloy. One skilled in the art may find additional applications for the apparatus, processes, systems, components, configurations, methods and applications disclosed herein. Thus, the illustration and description of the present invention, in context of an exemplary method for determining the extent of oxidation progression for a coated gas turbine blade or vane is merely one possible application of the present invention. However, the present invention has particular applicability for use as a method for determining the amount of oxidation by a metal turbine component coated with a coating without actual physical measurements or destructive analysis techniques.

Figure 1:
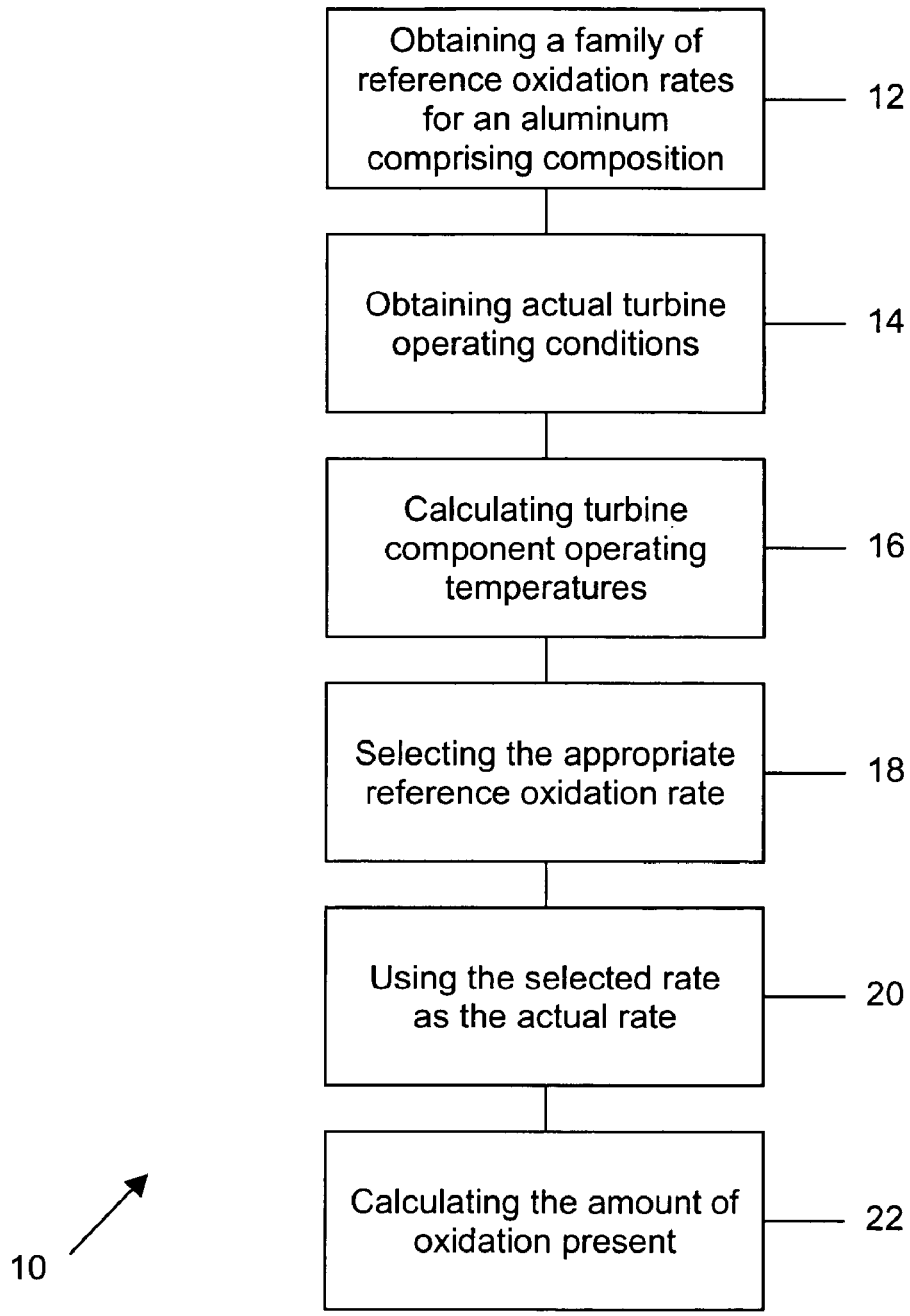
FIG. 1 is a flowchart illustrating a method for determining the extent of oxidation progression within a coated metallic turbine component.

Referring to FIG. 1, an exemplary flowchart 10 illustrating a method for determining the extent of an oxidation reaction of a coated metallic turbine component within a turbine is provided. In Step 1 of the method, as illustrated as reference number 12 and as explained in greater detail below, a family of reference oxidation rates are obtained for a coated system. In step 2, illustrated as reference number 14, a set of actual turbine operating conditions is obtained for the coated turbine components to calculate the thermal history of the coated component. Using more operating conditions may give a more accurate calculation of component temperature, while using fewer conditions may give a less accurate calculation of component temperature but allow for a more rapid calculation. Step 3, illustrated as reference number 16. Step 3 requires calculating the turbine component operating temperatures. Step 4, illustrated as reference number 18, is the selection of the appropriate reference oxidation rate curves from the family of reference oxidation rate curves. Step 5, illustrated as reference number 20, is using the selected reference oxidation reaction rates as the actual oxidation reaction rate. Step 6, illustrated as reference number 22, is a discrete summation of oxidation damage accumulation based on the path dependant phenomena, the overall result of the discrete summation is the calculation of the total amount of oxidation present. The amount of oxidation present is preferably determined by using the actual oxidation rate for the coated metal turbine component and the operating temperatures as a function of turbine operating conditions.

In an oxidation reaction, a material is oxidized thereby forming an oxidation or oxide layer. Over time, the oxide layer tends to spall, thereby exposing the substrate 40 (see FIG. 2b).

Figure 2A:
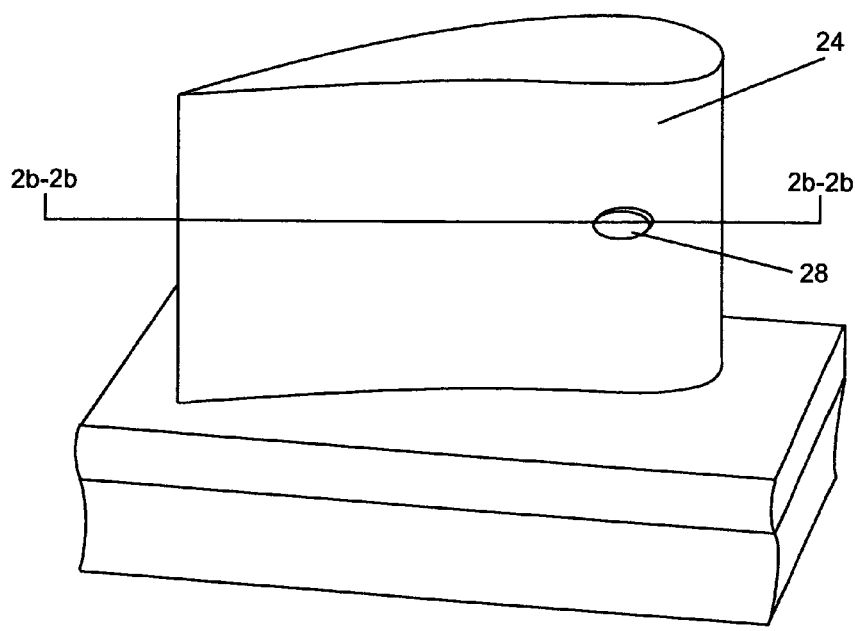
FIG. 2a shows an exemplary coated metallic turbine component.
Figure 2B:
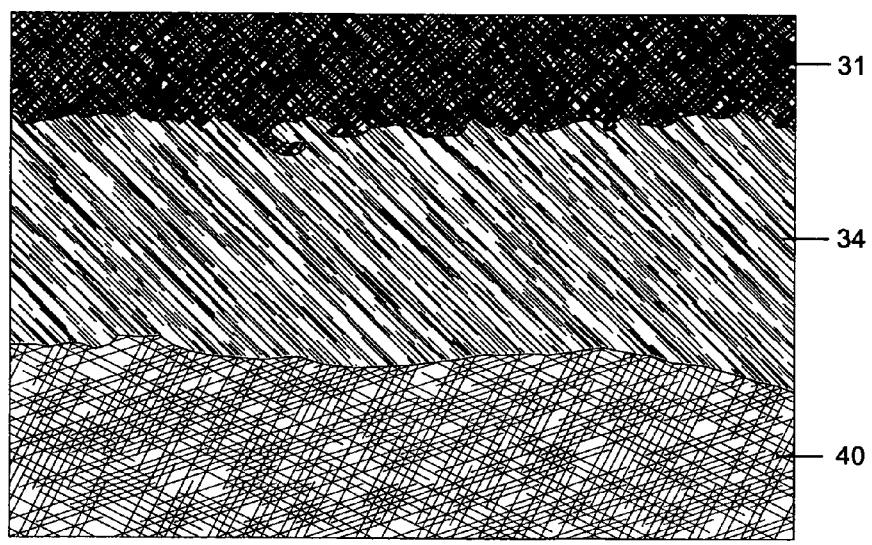
FIG. 2b is a detail cross sectional view along the cut 2b-2b of FIG. 2a showing a coating system.

FIG. 2a is a perspective view of an exemplary coated turbine component 24, and FIG. 2b is a detailed illustration of cross section 2b-2b of the coated turbine component 24. The coated turbine component 24 is typically comprised of the substrate 40, a bond coat 34, and a thermal barrier coating (TBC) 31. The substrate 40, bond coat 34, and TBC 31 are typically referred to as the coating system. However, it is known to those skilled in the art that the oxidizing component need not all three elements 31, 34, 40, and may include only one or more of such elements 31, 34, 40.

In the illustrated context of use, the substrate 40 is preferably a super-alloy metal. For example, the substrate 40 could be an equiaxed material, an inter-metallic material such as a titanium aluminide, or a non oxide ceramic matrix composite (CMC) such as the SiC—SiC type. However, those skilled in the art would readily appreciate that the substrate 40 could be any material suitable or useable for that particular context of use which is prone to oxidation under high temperature oxygen containing environments. Thus, the present invention is not limited to use with super-alloy metals.

The illustrated metallic coating 34 is, preferably, of MCrAlY composition. The composition of an MCrAlY bond coat 34 varies, as is recognized by those skilled in the art, however the bulk of the oxidation protection, or passivity, is derived from the presence of Aluminum to form a slow growing aluminum oxide layer on top of the metallic coating. McrAlY coatings comprise an appropriate metal or combinations of metal to form the matrix (M), a percentage of chromium (Cr), a percentage of Aluminum (Al), and a percentage of yittrium (Y). One skilled in the art would readily appreciate that any metallic component or metallic coated system 31, 34, 40 that undergoes an oxidation event upon elevated temperature exposure in an oxygen containing environment is suitable or useable for the particular context of use. For example, certain metallic systems may contain no aluminum or excess of chromium and therefore will form non-aluminum oxide oxidation products.

If an MCrAlY bond coat 34 is used, it can be comprised of a two phase composition of a cobalt chrome and nickel-rich matrix referred to as the gamma phase and a nickel and aluminum rich precipitate called the beta phase. It is recognized by those skilled in the art that the two phase diffusion aluminide structure mentioned above accounts for much of the oxidation resistant nature of the MCrAlY compositions. Therefore the use of a diffusion aluminide structure strongly influences the experimentally determined oxidation rate of the systems.

As oxidation progresses, the ability of the metallic system to remain passive decreases and over time, the TBC to bond coat interface will be weakened as well. Eventually TBC spallation typically results in increase of metal temperatures.

Figure 3:
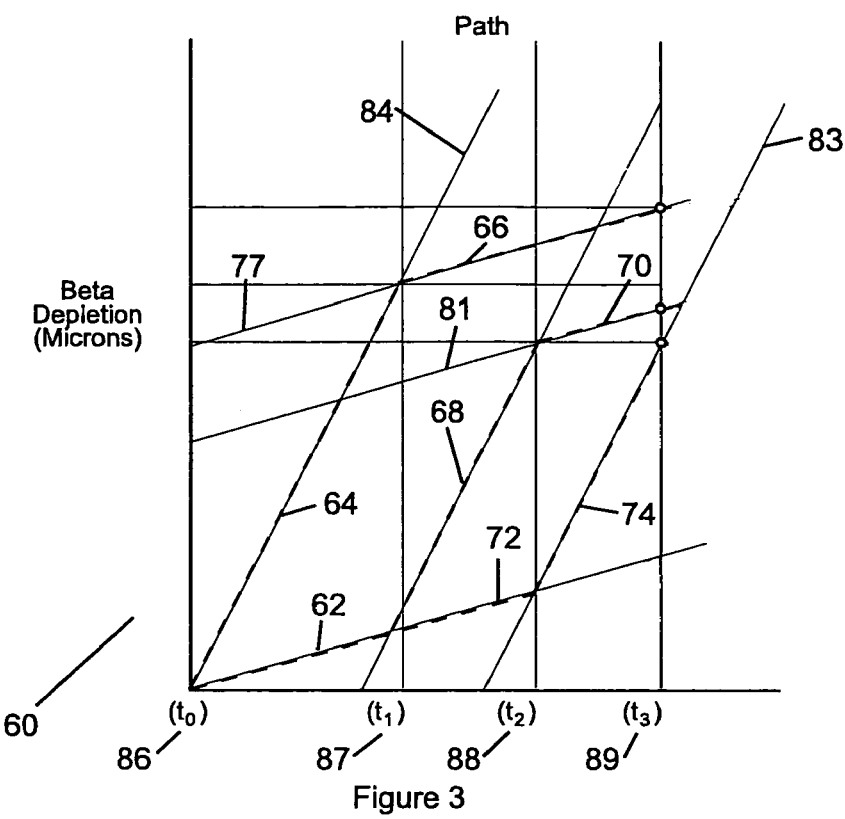
FIG. 3 shows a family of oxidation curves for the coated system determined at various temperature conditions.

FIG. 3 shows a plurality of path dependant oxidation rate summations based on two discrete linear oxidation rates. Three paths have been chosen for purpose of explanation. Overall path 64, 66 is formed by a first leg 64, with a high oxidation rate beginning at time $t_0$ 86 and temperature $T_2$ 84, extending to time t1 87, and then moving along a second leg 66 having a lower oxidation rate of the path 64, 66 at $t_1$ 87 and temperature $T_1$ 77, extending to time $t_3$ 89 and resulting oxidation damage. Another path 62, 72, 74, having a first leg 62, 72 with a low oxidation rate beginning at time to 86 and temperature $T_1$ 84, extending to time $t_2$ 88, and then moving along a second leg 74 with a higher oxidation rate of the path 62, 72, 74 from time $t_2$ 88 and temperature $T_2$ 83, extending to time $t_3$ 89. Another path 62, 68, 70, having a first leg 62 with a low oxidation rate beginning at time $t_0$ 86 and temperature $T_2$ 84, extending to time $t_1$ 87, and then moving along a second leg 68, having a higher oxidation rate of the path 62,68, 70 at time $t_1$ 87 and temperature $T_2$ 77, extending to time $t_2$ 88 and then moving along a third leg 70, having a lower oxidation rate of the path 62, 68, 70 from time $t_2$ 88 and back to temperature $T_1$ 81, extending to time $t_3$ 89. Furthermore, a path can be a portion of a larger following. For example, illustrated following 62, 68, 70 comprises legs oxidation rates 62, 68 which form path 62, 68 and legs 68, 70 which form path 68, 70. The similar time intervals and various summation rates of two oxidation rates dependant on temperature illustrates the path dependency of the total oxidation. The summation equation below encompasses the general result for the vector summation of accumulated oxidation damage in an MCrAlY coated turbine component system. It should be noted for other systems the general mathematical result may differ, however the path dependant nature of the summation process will not.

$$X_{SUM} = \sum_{i=1}^{i=n} [K(T_i)^*\Delta(t_i^{1/M})]$$

Where the vector definitions are:
$X_{SUM}$=Total Predicted Oxidation Damage Summation
$K(Ti)$=Oxidation Rate As a Function of Temperature
$\Delta(t_i^{1/M})$=time interval adjusted to the linear oxidation rate scale Each leg, or oxidation rate, in a path can be expressed as a particular mathematical expression. At least two different legs comprise a path and at least two legs in the path can be expressed by two non-equal mathematical expressions. However, as one skilled in the art will readily recognize, there is an infinite number of paths that can be formed and are as broad or restrictive as the turbine engine is operated and the path dependant vector summation of these linear rates can effect the final overall oxidation. A path is a plurality of legs meant to represent the temperature a coated turbine component is operating at during the operation cycle of the turbine.

Thus, it can be appreciated that the rate of depletion of beta phase is effected by the path and the effect that time and temperature have on the amount of beta depletion that occurs. FIG. 3 is an illustration of the path dependent nature of the beta phase depletion. That is, the amount of beta phase depletion is dependent on the time and temperature path (i.e. path dependent).

Figure 4:
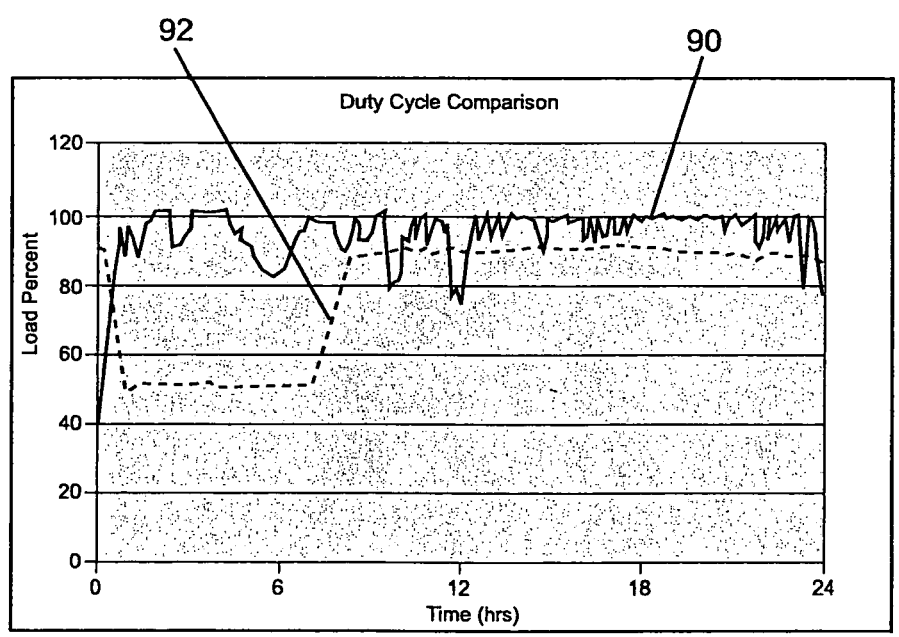
FIG. 4 shows two different operating conditions identifying two distinct operation loading and duty cycles resulting in two distinct thermal histories for the coated system within the same overall timeframe.

FIG. 4 shows an amount of variation in the operation of two exemplary turbines 90, 92 that can exist for a discrete period of time. It can readily be seen from this figure that if variations in operation from one turbine 90 to the next turbine 92 are not appropriately factored into the oxidation calculation, erroneous oxidation calculations can result. It can also be seen that within a given duty cycle turbine dynamics constantly fluctuate as a function of time, not factoring these fluctuations within a duty cycle can also lead to erroneous oxidation prediction. As previously discussed, there is a time and temperature path dependency with the calculation of extent of oxidation.

Figure 5:
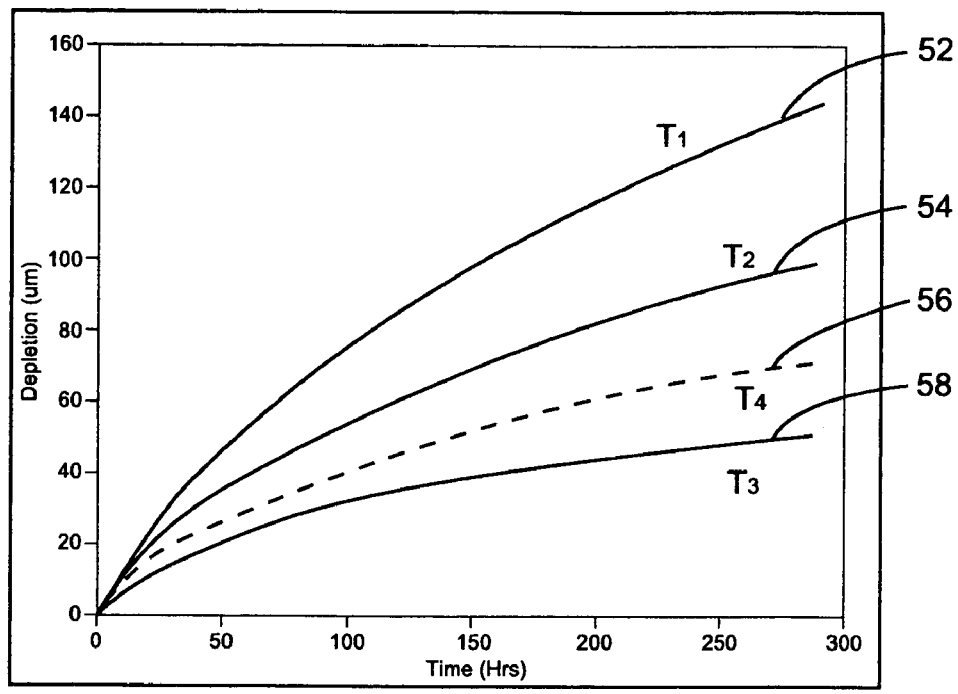
FIG. 5 is a graph illustrating the path dependent nature of the oxidation based on the experimentally determined linear oxidation rate.

As illustrated in FIG. 5, curves 52, 54, 58 comprise an exemplary family of oxidation rate curves from the same aluminum comprising material. Curve 52 being the oxidation rate curve for operating conditions resulting in temperature $T_1$, curve 54 being the oxidation rate curve for operating conditions resulting in temperature $T_2$ and curve 58 being the oxidation rate curve for operating conditions resulting in temperature $T_3$. The family is a plurality of data sets that can be in a mathematically well behaved equation, mathematically discretely defined equation, graphical or tabular form (e.g. the illustrated graph in a Cartesian coordinate system or a data matrix) that is calculated for a single material or material system and for at least one temperature. A clan of oxidation rate curves may also be comprised of several families of oxidation rate curves for a common material or material system as the overall material or material system degrades with exposure. For example, a family of oxidation rate curves applicable for a first degradation period may be combined with a family of oxidation rate curves for the same material or material system at a second degradation period. The family of oxidation rate curves are typically determined from practices such as experimental testing or actual use. In some instances, the family of reference oxidation rate curves may be presented as a single curve that is a function of temperature only wherein the reference oxidation-rate and the actual oxidation rate will match exactly.

The term curve is meant to encompass a data set presented in tabular form, matrix form, raw data, a regression fit of data, and the like. An Arrhenius relation can be used to create the oxidation curve as well as other mathematical relationships depending upon the mechanism of oxidation degradation as would be understood by those skilled in the art.

Referring to FIG. 5, an appropriate curve can be selected once turbine operation data has been obtained. An appropriate oxidation rate curve from the family of curves 52, 54, 58 is selected for use in determining an actual amount of oxidation present in a particular turbine component. This presently selected curve is based upon any one, or combination of the following: interpolation of at least one reference oxidation rate curve from the family of oxidation rate curves, extrapolation of at least one reference oxidation rate curve from the family of oxidation rate curves, selecting the reference oxidation rate curve that represents a "best fit" from the family of oxidation rate curves, a weighted average between a plurality of reference oxidation rate curves from the family of oxidation rate curves, matching portions of several oxidation rate curves for different temperature ranges from the family of oxidation rate curves to create a single curve. One skilled in the art will recognize that there are other acceptable methods to achieve the best fit that are not listed herein. The term "best fit" means that for each data point on the actual oxidation rate curve should be as close as possible in value to the corresponding data point on the reference oxidation rate curve. An acceptable limit for a value of a data point to be as close as possible would be for the actual oxidation rate and the reference oxidation rate to be preferably within 50% of each other, more preferably within 25% of each other and most preferably at the most within 10% of each other. However, there is no requirement that the curve determined to be the best fit be the curve selected. For example, the curve selected for curve 56 may be curve 58 or curve 52.

Turbine operating data can be interpreted and used by a processor in real time or non real time (within 30 seconds of real time). However, there is no requirement that the data needed for component temperature determination be collected continuously. Turbine operating data can also be obtained at the physical location of the turbine or at a remote collection point (e.g. monitoring station that receives turbine data from a plurality of turbines from across a region).

Figure 6:
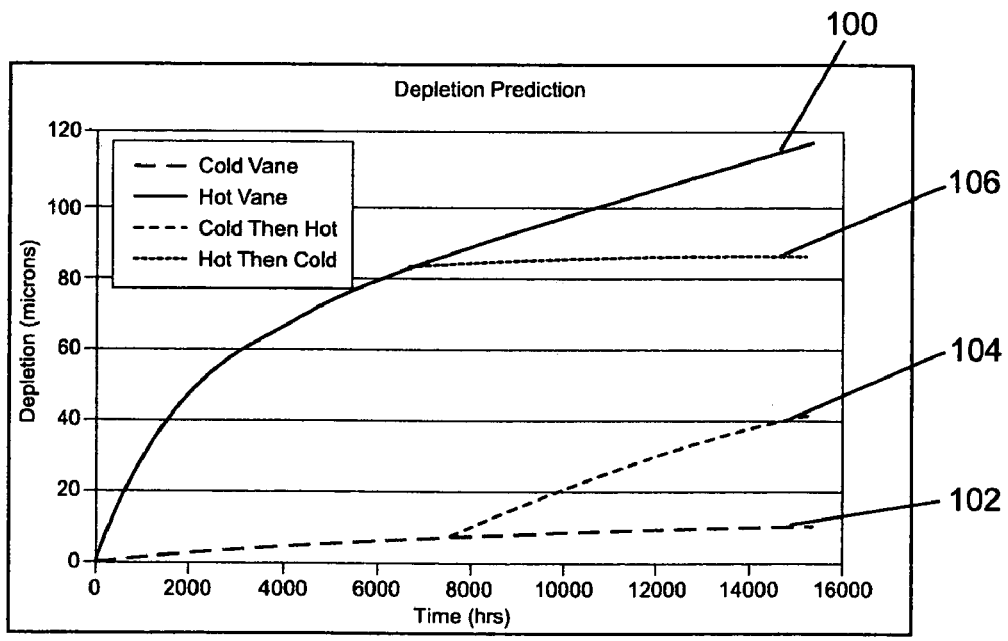
FIG. 6 shows turbine component effect of different duty cycles.

As seen in FIG. 6, the present invention can also assist in determining optimum duty cycles of the turbine components before the turbine components are exposed to operation. FIG. 6 illustrates the amount that oxidation progression can be changed by just altering the duty cycle of the component. For example, curve 102 depicts the amount of oxidation that a coated turbine component accumulates in a cooler duty cycle. Curve 104 depicts the amount of oxidation that a coated turbine a vane that was initially in a cool cuty cycle and later moved to a higher temperature duty cycle. Likewise, curves 100, 106 similarly show that there is a path dependency in the extent of oxidation as discussed above. Changing the duty cycle of turbine components during use or at service intervals can result in a calculable significant increase of expected life of the component.

While the preferred embodiments of the present invention have been shown and described herein, it will be obvious that such embodiments are provided by way of example only. Numerous variations, changes and substitutions will occur to those of skill in the art without departing from the invention herein. Also, one or more aspects or features of one or more embodiments or examples of the present invention may be used or combined with one or more other embodiments or examples of the present invention. Accordingly, it is intended that the invention be limited only by the spirit and scope of the appended claims.

We claim as our invention:

1. A method for determining the extent of an oxidation reaction of a coated metal turbine component within a turbine, comprising:
   providing an aluminum comprising coating on a metal substrate;
   providing a family of reference oxidation rate curves for the aluminum comprising coating as a function of time and temperature;
   calculating an actual oxidation rate for the aluminum comprising coating during operation of the turbine as a function of time or temperature;
   creating a path dependent oxidation rate curve based upon the calculated actual oxidation reaction rate;
   comparing the path dependent oxidation rate curve with the family of oxidation reaction rate curves;
   selecting from the family of reference oxidation reaction rate curves, a curve that generally corresponds with the path dependent oxidation rate curve; and
   using the selected curve and a summation of incremental amounts of the calculated actual oxidation reaction rate to approximate and makes available to a user the extent of oxidation of the coated turbine component.

2. The method as claimed in claim 1, wherein the aluminum coating is an MCrAlY coating.

3. The method as claimed in claim 1, wherein the metal substrate is a super-alloy.

4. The method as claimed in claim 1, wherein the step of obtaixiing the family of oxidation rate curves are determined for the same material.

5. The method as claimed in claim 4, wherein the step of obtaining theoxidation rate is calculated at a location on a turbine component selected from at least one point.

6. The method as claimed in claim 4, wherein the step of obtaining the extent of oxidatioir is a portion of the depleted operating life of the turbine component.

7. The method as claimed in claim 1, wherein the step of obtaining the actual oxidation reaction rate is calculated by an Arrhenius relation.

8. The method as claimed in claim 1, comprising a further step of calculating the oxidation rate at a plurality of locations on a turbine component that collectively comprise a region.

9. The method as claimed in claim 1, wherein the step of making the comparison of the family of oxidation reaction rate curves to the path dependent oxidation rate is based on a best fit relation.

10. The method as claimed in claim 1, wherein the step of obtaining the path dependent oxidation rate is within 50% of the actual oxidation rate.

11. The method as claimed in claim 1, wherein the step of obtaining the path dependent oxidation rate is within 25% of the actual oxidation rate.

12. The method as claimed in claim 1, wherein the step of obtaining the path dependent oxidation rate is within 10% of the actual oxidation rate.

13. The method as claimed in claim 1, further comprising a thermal barrier coating layer covering the aluminum coating.

14. The method as claimed in claim 13, wherein the step of obtaining the oxidation rate of the thermal barrier coating layer is calculated in a manner similar to the aluminum comprising bond coat.

15. The method as claimed in claim 1, wherein the turbine component is a turbine blade or vane.

16. The method as claimed in claim 1, wherein the extent of oxidation is used to clock a plurality of blades or vanes within the turbine.

17. A method for determining the extent of an oxidation reaction of a coated metallic turbine component within a turbine, comprising:
   determining a plurality of reference oxidation rates for a plurality of locations on the turbine component for a plurality of different turbine operating conditions;
   obtaining a set of actual turbine operating conditions based on time or temperature;
   obtaining a plurality of turbine component operating temperatures from the set of actual turbine operating conditions;
   selecting an appropriate reference oxidation rate curve from the plurality of reference oxidation rate curves based on the actual turbine operating conditions;
   using the selected reference oxidation rate curve as the actual oxidation rate curve;
   calculating an amount of oxidation present in the turbine component using the actual oxidation rate curve; and
   making available to a user the remaining life of the component based on calculated amount of oxidation,
   wherein the predicted amount of oxidation present is determined from the summation of an incremental calculated amount of oxidation from the set of actual operating conditions, and wherein the oxidation rate curve is a path dependent oxidation rate curve.

18. The method as claimed in claim 17, wherein the step of calculating the oxidation rate is performed in real time.

19. The method as claimed in claim 17, wherein the step of obtaining turbine operating conditions are obtained remotely.

20. The method as claimed in claim 17, comprising a further step of estimation of the amount of remaining operational life of the turbine component is at least partially based upon the amount of oxidation present in the component.

21. The method as claimed in claim 17, wherein the amount of oxidation present in the turbine component is calculated using the actual oxidation rate in a discrete path dependant calculation.

22. The method as claimed in claim 17, wherein the oxidation is a beta phase depletion.

23. A method of determining the extent of an oxidation reaction of a component, comprising:
   determining a plurality of oxidation rates;
   having or being provided one actual rate;
   selecting from a plurality of oxidation rate curves a curve that most closely matches to a curve representative of actual operating conditions; and
   using the curve to calculate the extent of oxidation of the component by incrementally summing the plurality of oxidation rates and wherein the oxidation rate curve is a path dependent oxidation rate curve; and making available to a user the calculated extend of oxidation of the component.

24. The method as claimed in claim 23, wherein the oxidation is a beta phase depletion.

* * * * *